United States Patent
Choi

(10) Patent No.: US 9,504,803 B2
(45) Date of Patent: Nov. 29, 2016

(54) CATHETER SET COMPRISING GUIDE WIRE

(71) Applicants: SEWOON MEDICAL CO., LTD., Cheonan-si, Chungcheongnam-do (KR); Sang-sik Choi, Seoul (KR)

(72) Inventor: Sang-sik Choi, Seoul (KR)

(73) Assignees: SEWOON MEDICAL CO., LTD., Cheonan-si, Chungcheongnam-do (KR); Sang-sik Choi, Seoul (KR)

(*) Notice: Subject to any disclaimer, the term of this patent is extended or adjusted under 35 U.S.C. 154(b) by 0 days.

(21) Appl. No.: 14/842,070

(22) Filed: Sep. 1, 2015

(65) Prior Publication Data

US 2015/0367100 A1    Dec. 24, 2015

Related U.S. Application Data

(62) Division of application No. 13/817,902, filed as application No. PCT/KR2010/006178 on Sep. 10, 2010, now Pat. No. 9,216,269.

(51) Int. Cl.
*A61M 25/00* (2006.01)
*A61B 17/34* (2006.01)
(Continued)

(52) U.S. Cl.
CPC ............ *A61M 25/0043* (2013.01); *A61B 5/05* (2013.01); *A61B 5/4893* (2013.01);
(Continued)

(58) Field of Classification Search
CPC .............. A61B 17/3401; A61B 17/3415; A61B 5/05; A61B 5/4893; A61B 5/6852; A61M 2025/0007; A61M 2025/0008; A61M 2025/09166; A61M 25/0043; A61M 25/09; A61N 1/0551; A61N 1/36017
See application file for complete search history.

(56) References Cited

U.S. PATENT DOCUMENTS 5,357,961 A    10/1994    Fields et al.
5,419,777 A    5/1995    Hofling
(Continued)

FOREIGN PATENT DOCUMENTS

EP    1002500 A1    5/2000
JP    2000-140132 A    5/2000
KR    20070027494 A    3/2007

OTHER PUBLICATIONS

International Search Report mailed Jul. 20, 2011; PCT/KR2010/006178.
(Continued)

*Primary Examiner* — Amanda Patton
(74) *Attorney, Agent, or Firm* — Ladas & Parry LLP

(57) ABSTRACT

The present invention relates to a catheter set for nerve treatment used for delivering a stimulus or a drug to nerves in the human body. According to the present invention, the catheter set for nerve treatment includes: a catheter capable of delivering a drug to a target nerve through a tube line, having a tube shape; a cylindrical cannula for supporting the catheter when inserted into the body tissue while slidably accommodating the catheter inside; a conductive guide wire to be accommodated inside the catheter, having one exposed end; and a conductive first stimulator connector for delivering an electric stimulus to the one exposed end of the guide wire, electrically connected to the other end of the guide wire. Therefore, it is possible to accurately place the end of the catheter at the location of the target nerve, to prevent the end of the catheter from deviating from the target nerve during an operation, and to finely adjust the location of the catheter even after removing the cannula.

10 Claims, 3 Drawing Sheets

(51) Int. Cl.
  *A61M 25/09* (2006.01)
  *A61N 1/05* (2006.01)
  *A61B 5/05* (2006.01)
  *A61B 5/00* (2006.01)
  *A61N 1/36* (2006.01)

(52) U.S. Cl.
  CPC ........ *A61B 5/6852* (2013.01); *A61B 17/3401* (2013.01); *A61B 17/3415* (2013.01); *A61M 25/09* (2013.01); *A61N 1/0551* (2013.01); *A61M 2025/0007* (2013.01); *A61M 2025/0008* (2013.01); *A61M 2025/09166* (2013.01); *A61M 2205/0233* (2013.01); *A61M 2205/0238* (2013.01); *A61N 1/36017* (2013.01)

(56) References Cited

U.S. PATENT DOCUMENTS 6,512,958 B1    1/2003   Swoyer et al.
6,978,180 B2   12/2005   Tadlock

OTHER PUBLICATIONS

USPTO NFOA dated Jun. 12, 2014 in connection with U.S. Appl. No. 13/817,902.
USPTO FOA dated May 8, 2015 in connection with U.S. Appl. No. 13/817,902.
USPTO NOA mailed Aug. 19, 2015 in connection with U.S. Appl. No. 13/817,902.

CATHETER SET COMPRISING GUIDE WIRE

TECHNICAL FIELD

The present invention relates to a catheter set for nerve treatment, and more particularly, to a catheter set for nerve treatment, which is used to operate neural blockade or neuromodulation through a drug or physical method to various nerves in the human body.

BACKGROUND ART

A medical treatment, such as diagnosis, therapy, anesthesia, or the like, may be performed in a method of inserting a tube-shaped catheter near nerve fibers of various nerve systems in the human body to inject various kinds of drugs.

To perform such a medical treatment using a catheter set for nerve treatment, it is important to find out an accurate location of a nerve to be treated and effectively deliver a drug to the found nerve.

FIGS. 1 and 2 show a conventional catheter set for nerve treatment, which is used for the purpose described above.

The conventional catheter set for nerve treatment includes an internal needle 1, a cannula 2, and a catheter 3.

The internal needle 1 is a conductive metal needle. The cannula 2 and the catheter 3 are flexible synthetic resin tubes, and the internal needle 1 is accommodated inside the cannula 2. When the internal needle 1 is completely inserted into the cannula 2, only a portion of the end of the internal needle 1 is exposed to the outside of the cannula 2. In a state where the internal needle 1 is connected to an electric stimulator (not shown), the internal needle 1 is assembled with the cannula 2 as shown in FIG. 1 and is inserted inside the body tissue as shown in FIG. 3.

The outermost part of nerve fibers of a nerve system in the human body is surrounded by a cylindrical membrane called as a neurovascular sheath 5 as shown in FIGS. 3 and 4, and various kinds of nerve bundles 6 and blood vessels 7 pass along inside the neurovascular sheath 5.

In a state where the internal needle 1 is connected to a nerve stimulation needle of the electric stimulator, the end of the internal needle 1, which is exposed outside the cannula 2, and the end of the cannula 2 are inserted into the neurovascular sheath 5 to approach near nerve fibers, and a nerve stimulation symptom is induced through an electric stimulus to detect a location of a nerve fiber to be treated. Since the internal needle 1 is made of a conductive metal, the internal needle 1 delivers the electric stimulus from the electric stimulator to nerves, and by observing a reaction of a patient in response to the electric stimulus, it is determined whether the internal needle 1 and the cannula 2 have arrived at a target nerve.

After placing the ends of the internal needle 1 and the cannula 2 at a nerve 6 to be treated in the method described above, the internal needle 1 is extracted in a state where the cannula 2 stays there, and the tubular catheter 3 is inserted near the nerve fiber through a tube line of the cannula 2 as shown in FIGS. 2 and 4.

After the catheter 3 is completely inserted inside the cannula 2, the cannula 2 is extracted in a state where the catheter 3 stays there, and a drug is injected through an inner tube of the catheter 3 to continuously operate neural blockade or neuromodulation.

For example, a drug for alleviating a pain may be injected through the catheter 3 to alleviate a pain of a patient, an anesthetic may be injected through the catheter 3 to anesthetize a target nerve, and a drug may be injected to an adherent nerve part with a pressure through the catheter 3 to solve the adhesion of a target nerve.

However, since the catheter 3 is made of a very flexible material, in a process of a medical treatment using the conventional catheter set for nerve treatment as described above, the end of the catheter 3 may be located at a deviated place from a target nerve firstly found using the internal needle 1, thereby decreasing a treatment effect.

That is, even though the end of the catheter 3 is firstly located near the target nerve, in a process of extracting the internal needle 1 from the cannula 2, inserting the catheter 3 inside the cannula 2, and extracting the cannula 2 from the body tissue in a state where the catheter 3 stays there, such a problem that the end of the catheter 3 moves to a place apart from the target nerve occurs frequently. In this case, since a drug injected through the catheter 3 does not affect the target nerve, a treatment effect may be deteriorated, or a medical treatment may fail.

In addition, as shown in FIG. 3, when the end of the internal needle 1 is inserted inside the neurovascular sheath 5 while the end of the cannula 2 cannot be inserted inside the neurovascular sheath 5 by being caught by the outer wall of the neurovascular sheath 5, it is determined in the outside that the cannula 2 has arrived at the target nerve 6. However, as shown in FIG. 4, when the internal needle 1 is extracted, and the catheter 3 is inserted inside the cannula 2, since the catheter 3 is made of a flexible material and has a blunt end, the catheter 3 may not be inserted inside the neurovascular sheath 5 so that a drug cannot be delivered to the nerve 6, thereby frequently causing a treatment failure.

Meanwhile, the cannula 2 is made of a very flexible and smooth material to prevent a nerve damage. Therefore, if the internal needle 1 is inserted inside the cannula 2 several times to increase accuracy of a medical treatment, the end of the cannula 2 may be frequently damaged and torn by the internal needle 1. When the end of the cannula 2 is torn by the internal needle 1, it is more difficult than before to insert the cannula 2 inside the neurovascular sheath 5, thereby increasing the possibility of a treatment failure.

In addition, when a nerve treatment is performed using the catheter set for nerve treatment as described above, since the internal needle 1 is extracted to insert the catheter 3, it cannot be checked during injection of a drug whether the end of the catheter 3 is located near the target nerve, even when the catheter 3 is gradually inserted inside the tissue with a force to correct a location of the catheter 3, it cannot be checked whether the location of the catheter 3 approaches the target nerve. In this case, although a location of the catheter 3 may be detected in a method of checking an image projected by injecting contrast media through the catheter 3 and scanning radiation, this method has problems in that a patient is exposed to the radiation, it is difficult to determine an effect, it takes too much time and cost, and it is troublesome to perform the method.

DETAILED DESCRIPTION OF THE INVENTION

Technical Problem

The present invention provides a catheter set for nerve treatment, of which a structure is improved not to damage a cannula even after several operations and to detect a location of the end of a catheter by using a nerve stimulator even in a state where the cannula is removed, to solve such a difficulty that the end of a catheter cannot be located at a correct position of a target nerve and such a problem that a position of the end of the catheter is deviated from the target nerve even during an operation.

Technical Solution

According to an aspect of the present invention, there is provided a catheter set for nerve treatment, including: a catheter capable of delivering a drug to a target nerve through a tube line, having a tube shape; a cylindrical cannula for supporting the catheter when inserted into the body tissue while slidably accommodating the catheter inside; a conductive guide wire to be accommodated inside the catheter, having one exposed end; and a conductive first stimulator connector for delivering an electric stimulus to the one exposed end of the guide wire, electrically connected to the other end of the guide wire.

On the guide wire, a standard graduation corresponding to a length obtained by adding a length of an exposed end of the guide wire to the whole length of the catheter may be marked, and reference graduations may be marked around the standard graduation to identify a sliding distance of the guide wire inside the catheter.

The one end (tip) of the guide wire may be formed straight, or the one end (tip) of the guide wire may be formed to be bent in one direction so that one end of the catheter is located at a desired part when the catheter is inserted inside the body tissue.

One end of the cannula may have conductivity, an outer circumference of the cannula except for the one end may be coated with an electrical insulation material, and the catheter set may further include a conductive second stimulator connector for delivering an electric stimulus to the one end of the cannula, electrically connected to the other end of the cannula.

Advantageous Effects

According to the present invention, by improving a structure of a catheter set for nerve treatment, the end of a catheter may be located as a correct position of a target nerve, the location of the end of the catheter is not deviated from the target nerve even during an operation, a cannula is not damaged even after several operations, it is possible to detect the location of the end of the catheter by using a nerve stimulator and radiation irradiation even in a state where the cannula is removed, and it is possible to finely adjust the location of the catheter even after the cannula is removed.

BEST MODE

Mode of the Invention

Before describing embodiments of the present invention, the technical contents related to a nerve block to which embodiments of the present invention are applied will be schematically described. The nerve block is largely divided into a peripheral nerve block and a central nerve block (an epidural nerve block and an intrathecal nerve block). In addition, the nerve block may be divided into a one-time nerve block and a continuous nerve block according to an acting time. The one-time nerve block is to inject a drug only one time after a cannula for block is inserted near a target nerve, and the continuous nerve block is to maintain a block state for a long time by continuously injecting a drug after a cannula for block is inserted near a target nerve and a catheter is slid through the cannula.

Hereinafter, various embodiments of the present invention are described with reference to the accompanying drawings. Two ends exist in each member of a catheter set according to embodiments of the present invention with respect to the drawings, wherein, for convenience of description, an end of each member inserted inside the body tissue is called one end, and an end located in the opposite direction is called the other end.

Figure 5A:
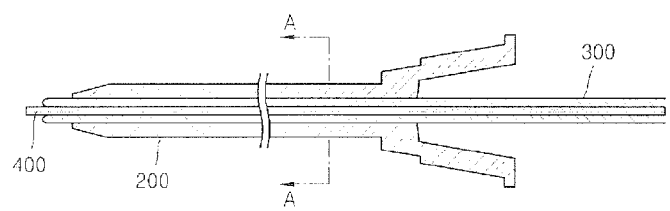
FIG. 5A is a cross-sectional view of a catheter set for nerve treatment in which a guide wire is included, according to an embodiment of the present invention.

FIG. 5A is a cross-sectional view of a catheter set for nerve treatment in which a guide wire 400 is included, according to an embodiment of the present invention. The catheter set according to the current embodiment may include a cannula 200 located at the outermost thereof, a catheter 300 accommodated inside the cannula 200, the guide wire 400 accommodated inside the catheter 300, and a stimulator connector (not shown).

Figure 1:
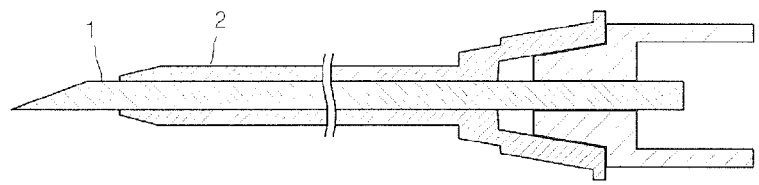
FIG. 1 is a cross-sectional view of an assembly of an internal needle and a cannula in a conventional catheter set for nerve treatment.

The cannula 200 has a cylindrical shape and is inserted inside the body tissue while slidably accommodating the catheter 300 inside. Since the catheter set according to the current embodiment does not have the internal needle 1 as shown in FIG. 1, the cannula 200 needs to have a strength enough to support the the catheter 300 accommodated inside the cannula 200 so as for the catheter set to be inserted up to a target nerve through the body tissue. Therefore, it is preferable that the cannula 200 is made of a metal or a solid material having a strength that is equivalent to the metal. Of course, a method of inserting the cannula 200, which accommodates an internal needle inside, into the body tissue may also be used in accordance with circumstances.

The catheter 300 has a tubular shape to be able to deliver a drug to a target nerve through a tube line and is made of a flexible material. Therefore, even though the cannula 200 is removed after the cannula 200, which accommodates the catheter 300 inside, is inserted into the body tissue, a drug may be continuously delivered to a target nerve through the catheter 300.

The guide wire 400 is conductive and is slidably accommodated inside the catheter 300, wherein it is preferable that the guide wire 400 is accommodated to expose one end (tip) of the guide wire 400 in a catheter direction inserted inside the body tissue. Although the guide wire 400 is flexible, the guide wire 400 has relatively greater solidity than the catheter 300. That is, even though the cannula 200 is removed after the catheter set according to the current embodiment is inserted into the body tissue, the guide wire 400 exists inside the catheter 300 still inserted inside the tissue, and thus the catheter 300 is supported. The guide wire 400 is made of a metallic material through which an electric current can flow.

This method is particularly useful in a case where an operation is performed in a state where the guide wire 400 is inserted inside the tube of the catheter 300 so that the catheter 300 can be easily inserted up to a target nerve located far from the skin. That is, the catheter 300 may be inserted up to a target nerve located at a deep place of the body tissue in a method of adding a force to the guide wire 400 in a state where the catheter 300 made of a flexible and smooth material is supported by using the guide wire 400.

The stimulator connector (not shown) is conductive and is electrically connected to the other end of the guide wire 400. The stimulator connector is electrically connected to a typical nerve stimulator (not shown) to apply an electric current through the guide wire 400. That is, an electric current generated by the nerve stimulator is delivered to the guide wire 400 via the stimulator connector, and an electric stimulus is applied to a target nerve through the guide wire 400 exposed at the one end of the catheter set according to the current embodiment. Therefore, according to embodiments of the present invention, the guide wire 400 functions to support the catheter 300 made of a smooth material and also functions as a cable through which an electric current flows. The catheter set may have a simple structure and allow manufacturing costs to be reduced by delivering an electric stimulus through the guide wire 400.

When the cannula 200 accommodating an internal needle inside is inserted inside the body tissue, to apply an electric stimulus to a target nerve according to an embodiment of the present invention, the internal needle may be first removed, and an assembly of the catheter 300 and the guide wire 400 may be slidably inserted inside the cannula 200.

Figure 2:
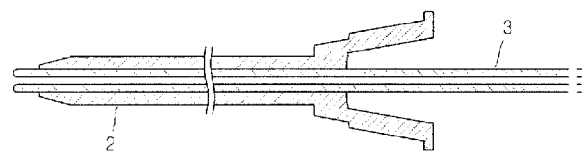
FIG. 2 is a cross-sectional view of an assembly of a catheter and the cannula without the internal needle in the conventional catheter set for nerve treatment of FIG. 1.

Unlike the prior art as described above with reference to FIGS. 1 and 2, in the current embodiment of FIG. 5A, an electric stimulus used to determine whether an assembly of the cannula 200, the catheter 300, and the guide wire 400 is inserted inside the body tissue and a cannula set has arrived at a target nerve desired by an operator is applied through the guide wire 400. Therefore, it is preferable that one end of the cannula is sharply formed to be able to be inserted through the body tissue. A more concrete operating method using the catheter set will be described below.

Figure 5B:
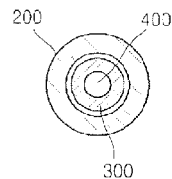
FIG. 5B is a cross-sectional view of line A-A of the catheter set for nerve treatment of FIG. 5A.

FIG. 5B is a cross-sectional view of line A-A of the catheter set for nerve treatment of FIG. 5A.

The cannula 200 located at the outermost of the catheter set, the catheter 300 accommodated inside the cannula 200, and the guide wire 400 accommodated inside the catheter 300 are sequentially shown.

As described above, the guide wire 400 is made of a conductive metal capable of applying an electric stimulus to a target nerve by receiving an electric current from the nerve stimulator (not shown). Since the cannula 200 in the catheter set functions as a kind of a needle capable of penetrating the body tissue, a metallic material may be selected for the cannula 200. In this case, an electric stimulus should be delivered only through the one end of the catheter set at which the guide wire 400 is exposed, but nevertheless it may be worried that an electric current is also delivered to the cannula 200 made of a metal, thereby resulting in an incorrect diagnosis. However, since the catheter 300 made of a synthetic resin exists between the guide wire 400 and the cannula 200, the possibility that such a problem occurs is removed. Therefore, it is preferable that the catheter 300 is made of an insulation material.

Figure 6:
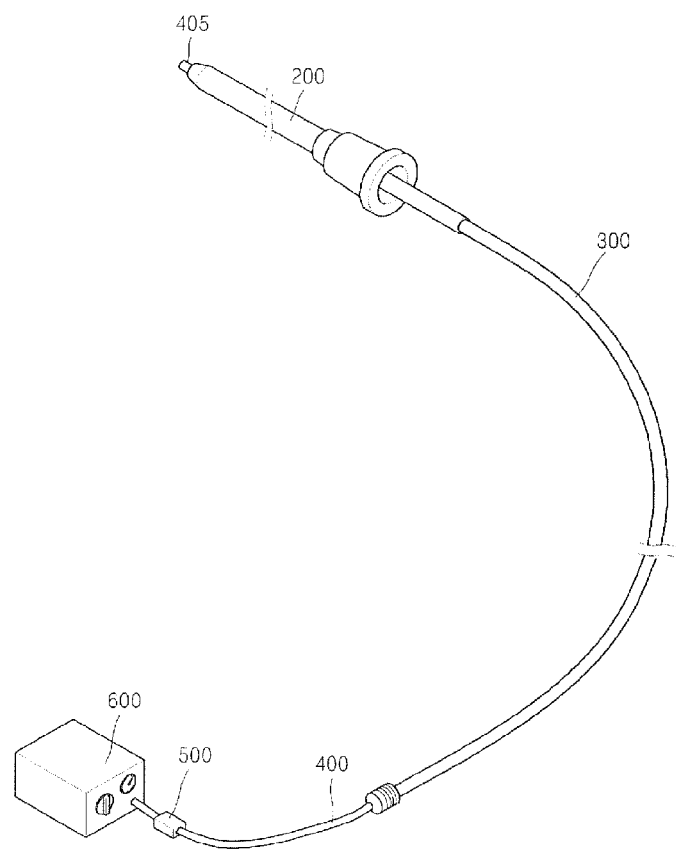
FIG. 6 illustrates a catheter set for nerve treatment in which the guide wire is included, to which a nerve stimulator is connected, according to an embodiment of the present invention.

FIG. 6 illustrates a catheter set for nerve treatment in which the guide wire 400 is included, to which a nerve stimulator 600 is connected, according to an embodiment of the present invention.

The catheter set for nerve treatment according to the current embodiment may include the cannula 200, the catheter 300 accommodated inside the cannula 200 while extending long from the other end of the cannula 200, the guide wire 400 accommodated inside the catheter 300 while being exposed from the one end of the catheter 300, and a stimulator connector 500 electrically connected to the other end of the guide wire 400. In addition, FIG. 6 also shows a nerve stimulator 600 electrically connected to the stimulator connector 500 to supply an electric current to the stimulator connector 500.

First, when the nerve stimulator 600 generates an electric current and supplies the electric current to the conductive guide wire 400 via the conductive stimulator connector 500, the supplied electric current is finally delivered to a target nerve through one end 405 of the guide wire 400.

Figure 7A:
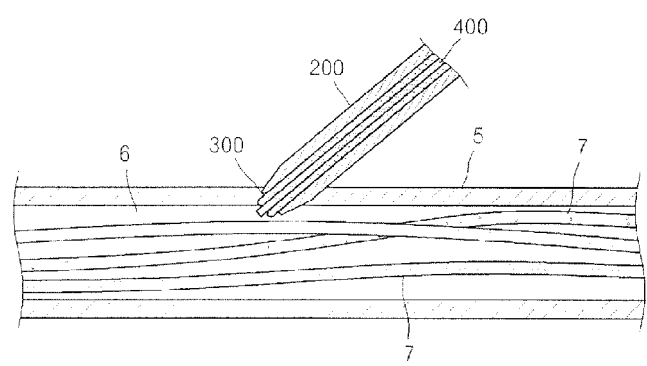
FIGS. 7A and 7B are illustrations for describing a process of an operation using a catheter set for nerve treatment in which the guide wire is included, according to an embodiment of the present invention.
Figure 7B:
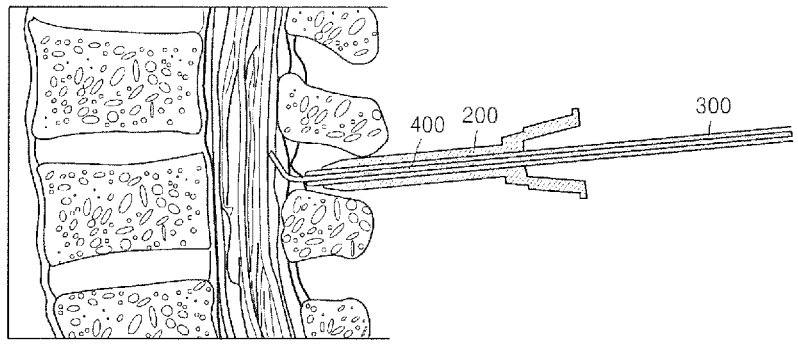

FIGS. 7A and 7B are illustrations for describing a process of an operation using a catheter set for nerve treatment in which the guide wire 400 is included, according to an embodiment of the present invention, and the process will be sequentially described below.

FIG. 7A assumes a situation in which a location of a target nerve 6 is found by inserting the catheter set inside the body tissue and the target nerve 6 is blocked. It is assumed that a nerve stimulator (not shown) is electrically connected to the other end of the catheter set through a stimulator connector (not shown).

An operator inserts the catheter set inside the body tissue by considering a location of a target nerve 6. Since the target nerve 6 exists under skin tissue, the target nerve 6 cannot be checked with naked eyes. Therefore, the operator may check whether one end (tip) of the catheter set is located near the target nerve 6 desired by the operator, by operating the nerve stimulator connected to the catheter set to deliver an electric stimulus. For example, if the target nerve 6 is a nerve related to muscles in a right arm, when the one end of the catheter set is located near the target nerve 6, the muscles in the right arm react in response to the electric stimulus, and the operator visually recognizes the reaction.

If it is determined that the one end of the catheter 300 has arrived near the target nerve 6, the operator may remove the cannula 200 from the catheter set. Even though a fine location adjustment is required to find a more accurate location near the target nerve 6, since the guide wire 400 still exists inside the catheter 300, a location of the target nerve 6 may be detected through an electric stimulus. That is, a location of the one end of the guide wire 400 corresponds to a location of the one end of the catheter 300.

Figure 3:
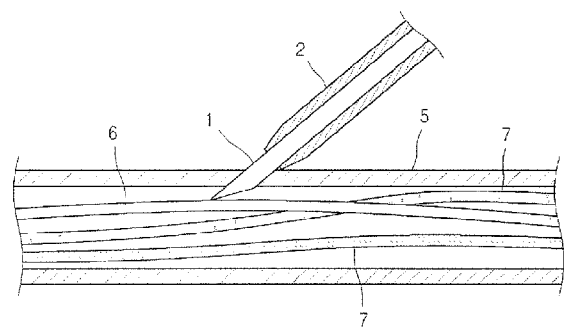
FIGS. 3 and 4 cross-sectional views for describing a process of an operation using the conventional catheter set for nerve treatment of FIG. 1.
Figure 4:
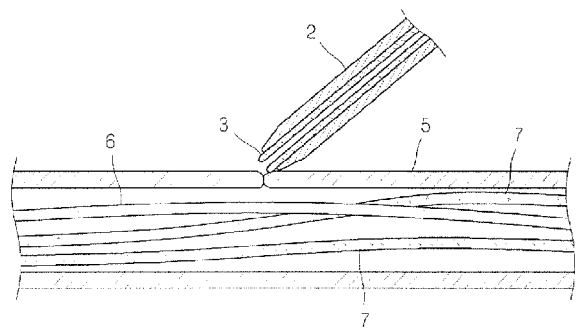

If it is determined that the one end of the catheter 300 is accurately located near the target nerve 6, the operator may also remove the guide wire 400 accommodated inside the catheter 300. In this case, only the catheter 300 remains inside the body tissue, and a treatment or anesthesia drug may be accurately supplied to the target nerve 6 through a tube formed inside the catheter 300. Therefore, this structure is differentiated from the conventional cannula 2 shown in FIG. 3 and the conventional catheter 3 shown in FIG. 4, and in the embodiment of the present invention, which is shown in FIG. 7A, since a drug injected through the catheter 300 is effectively injected to the target nerve 6, an operation effect desired by the operator may be more accurately displayed.

In FIG. 7A, it will be understood that an operation may be performed by inserting the cannula 200 with an internal needle (not shown) inside instead of the catheter 300 into the body tissue, removing the internal needle, and slidably inserting the catheter 300 and the guide wire 400 inside the cannula 200 for convenience of the operation.

FIG. 7B assumes an epidural nerve block performed for a painless delivery in a maternity course. Conventionally, an epidural space is found for such an epidural nerve block by using a Loss of Resistance (LOR) method using a syringe based on experiences of an operator. The LOR method is to find an epidural space by using the matter that air in a syringe is easily injected in an epidural space with rough tissue while air in a syringe is not easily injected in tight tissue around the backbone. However, such a method only depends on experiences of an operator and is not easy for non-experts who lack experiences.

In this case, when the catheter set proposed as an embodiment of the present invention is used, the following procedures are performed. First, an operator inserts the catheter set between vertebras. When the cannula 200 is inserted between the vertebras, an electric current is applied through a nerve stimulator (not shown) connected to the other end of the guide wire 400. While visually recognizing a reaction of the human body in response to the electric current, the operator may check whether the one end of the catheter set has accurately arrived at a target nerve. If the operator confirms that the one end of the catheter set has accurately arrived near the target nerve, the operator may remove the cannula 200. To more accurately fine a location of the target nerve, an electric stimulus may be applied while slightly moving the catheter 300. If an accurate location of the target nerve is detected by repeatedly performing this procedure, the guide wire 400 may also be removed to inject a drug through a tube formed inside the catheter 300.

Although FIG. 7B is an illustration for a central nerve block, the following configuration is additionally proposed for a case where the catheter set according to an embodiment of the present invention is used for a peripheral nerve block.

In the catheter set, the one end of the cannula 200 has conductivity and is electrically connected to the other end of the cannula 200, and the outer circumference of the cannula 200 except for the one end is coated with an electrical insulation material. In addition, the catheter set may further include a conductive stimulator connector for delivering an electric stimulus to the one end of the cannula 200 to apply an electric stimulus through the cannula 200 besides the guide wire 400 described above. Of course, a nerve stimulator will be connected to the stimulator connector. The cannula 200 is preferably made of a conductive metal, but the remaining portion (outer circumference) except for the one end of the cannula 200 should be coated with an electrical insulation material to prevent an electric stimulus from being delivered to neighboring nerves through the whole cannula 200. Accordingly, an electric stimulus is delivered only through the one end of the cannula 200. This structure may be specifically usefully used in an environment, such as a peripheral nerve, for which it is difficult to use the LOR method.

For example, an operator first inserts the cannula 200, which has conductive one end and accommodates only an internal needle inside, inside the body tissue. In this state, the operator supplies an electric current generated by a nerve stimulator to a nerve part through a conductive stimulator connector electrically connected to the other end of the cannula 200. By doing as so, the operator may find a target nerve even at a peripheral nerve part having no air resistance. If it is determined that the one end of the cannula 200 has arrived near the target nerve, the operator removes the internal needle accommodated inside the cannula 200 and slidably inserts an assembly of the catheter 300 and the guide wire 400 inside the cannula 200. The operator may finely search for the target nerve by applying an electric stimulus through the inserted guide wire 400.

Meanwhile, a method of effectively detecting an insertion location of a catheter set in such an operation process will be described below. As described above, the guide wire 400 is made of a conductive metal. Therefore, when the catheter set is inserted inside the body tissue, an operator may visually recognize a figure of the catheter set inserted inside the body tissue through radiation irradiation.

As described above, even though an operator is not an expert, the operator may more easily find a location of a target nerve and inject a proper drug through the catheter set for nerve treatment according to an embodiment of the present invention. In addition, by visually recognizing a location of the metallic guide wire 400 through radiation irradiation, treatment and anesthesia operations can be more easily performed. In addition, unlike the operation method of FIG. 3, since the guide wire 400 is slidably accommodated inside the catheter 300 instead of a sharp internal needle in FIGS. 7A and 7B, the cannula 200 or the catheter 300 is not damaged even after several operations.

Figure 8A:
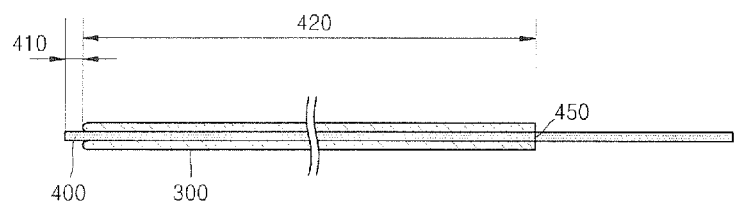
FIGS. 8A and 8B are illustrations for describing graduations marked on a catheter set for nerve treatment in which the guide wire is included, according to an embodiment of the present invention.
Figure 8B:
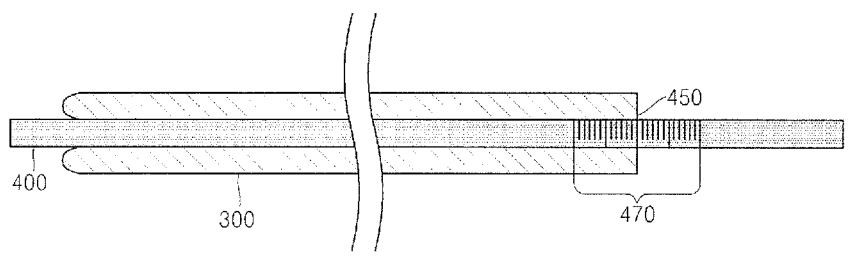

FIGS. 8A and 8B are illustrations for describing graduations marked on a catheter set for nerve treatment in which the guide wire is included, according to an embodiment of the present invention.

The catheter set according to the current embodiment has a premise that a length of the catheter 300 is almost the same as a length of the guide wire 400 exposed at one end of the catheter 300. Of course, it is reasonable for an electric stimulus that the length of the guide wire 400 is somewhat longer than the length of the catheter 300. Therefore, according to the embodiment of the present invention, which is shown in FIGS. 8A and 8B, it is preferable that a standard graduation 450 corresponding to a length obtained by adding a length 410 of exposed one end of the guide wire 400 to the whole length 420 of the catheter 300 is marked on the guide wire 400, because an assembled location of the guide wire 400 may somewhat vary through an insertion process even though the guide wire 400 is assembled with the catheter set to expose the one end there of a little before the catheter set is inserted inside the body tissue or only the guide wire 400 may be slidably moved inside the catheter 300 after the insertion. The standard graduation 450 is a means for allowing an operator to visually recognize a position relationship between the other end of the catheter 300, which is exposed outside the skin, and the guide wire 400.

FIG. 8B shows reference graduations 470 marked around the standard graduation 450 on the guide wire 400 to more easily identify a sliding distance of the guide wire 400 inside the catheter 300. An operator may visually recognize through the reference graduations 470 how much deeper or shallower the guide wire 400 is inserted based on the standard graduation 450. The reference graduations 470 are preferably marked to the left and the right by about 3 cm each with 0.5-mm gaps based on the standard graduation 450.

Throughout the embodiments described above, the length of the guide wire 400 exposed at the one end of the catheter 300 may vary according to the magnitude of an electric current supplied to the guide wire 400, but it is preferable that about 0.5 mm is exposed in a typical environment. In addition, when an electric current supplied by a nerve stimulator is about 0.3 mA, it is experimentally known that nerves within a range of about 1 mm from the one end of the guide wire 400 receive a stimulus. However, since the exposed length of the guide wire 400 and the range within which nerves may receive a stimulus may vary according to a patient or a material of the guide wire 400, the values may be changed to proper values by one of ordinary skill in the art.

Figure 9:
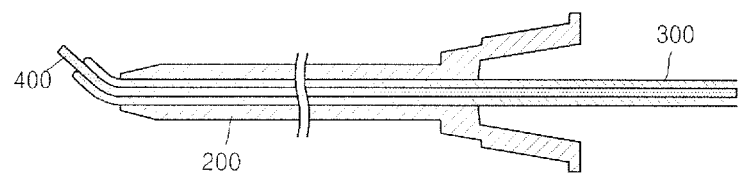
FIG. 9 illustrates a catheter set for nerve treatment in which a guide wire, one end of which is bent in one direction, is included, according to another embodiment of the present invention.

FIG. 9 illustrates a catheter set for nerve treatment in which the guide wire 400, one end of which is bent in one direction, is included, according to another embodiment of the present invention.

While the catheter 300 and the guide wire 400 are formed straight in the embodiment of FIG. 5A, one end of the guide wire 400 of FIG. 9 is bent in a specific direction, and the catheter 300 supported by the guide wire 400 is also bent in the same direction. Therefore, an operator may adjust the catheter set so that one end of the catheter 300 is located at a desired part when the catheter 300 is inserted inside the body tissue. That is, the operator may select a straight shape or a bent shape of the guide wire 400 in accordance with an operation part and circumstances, and when the operator selects the bent shape of the guide wire 400, the operator may optionally select one of guide wires 400 bent with various angles and shapes.

Although an operation is easily performed only with the straight guide wire 400 for a general peripheral nerve block, when an operation is performed by optionally selecting both the bent and straight guide wires 400 for a central nerve block, in particular, an epidural nerve block, more convenience may be provided to the operator.

Specifically, by using the bent guide wire 400, an operator may visually recognize stimulus aspects and more accurately diagnose a lesion part by applying an electric stimulus while slightly moving one end of the bent guide wire 400 in a state where the catheter set is inserted inside the body tissue.

While the present invention has been particularly shown and described with reference to exemplary embodiments thereof, it will be understood by those of ordinary skill in the art that various changes in form and details may be made therein without departing from the spirit and scope of the present invention as defined by the following claims. The exemplary embodiments should be considered in descriptive sense only and not for purposes of limitation. Therefore, the scope of the present invention is defined not by the detailed description of the present invention but by the appended claims, and all differences within the scope will be construed as being included in the present invention.

The invention claimed is:

1. A catheter set for nerve treatment, which is used to deliver a stimulus or a drug to a nerve of the human body, comprising:
   a catheter capable of delivering a drug to a target nerve through a tube line, having a tube shape;
   a cylindrical cannula for supporting the catheter when inserted into the body tissue while slidably accommodating the catheter inside;
   a conductive guide wire to be accommodated inside the catheter, having one exposed end, wherein the exposed end of the conductive guide wire is bent in a predetermined direction; and
   a conductive first stimulator connector for delivering an electric stimulus to the one exposed end of the guide wire, electrically connected to the other end of the guide wire.

2. The catheter set of claim 1, wherein the cannula is made of a metal.

3. The catheter set of claim 2, wherein the catheter is made of a synthetic resin insulating the catheter from the metal cannula.

4. The catheter set of claim 1 wherein the guide wire has greater solidity than the catheter.

5. The catheter set of claim 1, wherein one end of the cannula is sharply formed to enable insertion through body tissue.

6. The catheter set of claim 1, wherein, on the guide wire, a standard graduation corresponding to a length obtained by adding a length of an exposed end of the guide wire to the whole length of the catheter is marked.

7. The catheter set of claim 6, wherein reference graduations are marked around the standard graduation on the guide wire to identify a sliding distance of the guide wire inside the catheter.

8. The catheter set of claim 1, wherein the one end of the guide wire is formed to be bent in one direction so that a location of one end of the catheter is adjusted when the catheter is inserted inside the body tissue.

9. The catheter set of claim 1, wherein the guide wire is made of a metallic material to identify a figure of the guide wire inserted inside the body tissue through radiation irradiation.

10. The catheter set of claim 1, wherein the electric stimulus is delivered to the exposed end of the conductive guide wire when the catheter set is located near the target nerve.

\* \* \* \* \*